(12) United States Patent
Chen et al.

(10) Patent No.: US 9,012,192 B2
(45) Date of Patent: *Apr. 21, 2015

(54) ULTRASOUND ENHANCED GROWTH OF MICROORGANISMS

(75) Inventors: Jie Chen, Edmonton (CA); James Xing, Edmonton (CA); Woon T. Ang, Edmonton (CA)

(73) Assignee: Intelligentnano Inc., Edmonton, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/238,978

(22) Filed: Sep. 21, 2011

(65) Prior Publication Data

US 2012/0100525 A1    Apr. 26, 2012

Related U.S. Application Data

(63) Continuation-in-part of application No. 13/060,860, filed as application No. PCT/CA2009/001189 on Aug. 26, 2009.

(60) Provisional application No. 61/091,830, filed on Aug. 26, 2008.

(51) Int. Cl.
| | |
|---|---|
| *C12P 1/00* | (2006.01) |
| *C12N 13/00* | (2006.01) |
| *C12N 1/14* | (2006.01) |
| *C12N 1/18* | (2006.01) |
| *C12P 7/06* | (2006.01) |
| *C12P 17/04* | (2006.01) |
| *C12P 19/02* | (2006.01) |
| *C12P 19/14* | (2006.01) |
| *C12M 1/42* | (2006.01) |

(52) U.S. Cl.
CPC ...... *C12N 13/00* (2013.01); *C12N 1/14* (2013.01); *C12N 1/18* (2013.01); *C12P 7/06* (2013.01); *C12P 17/04* (2013.01); *C12P 19/02* (2013.01); *C12P 19/14* (2013.01); *Y02E 50/17* (2013.01); *C12M 35/04* (2013.01)

(58) Field of Classification Search
CPC ............ C12P 1/02; C12P 1/06; C12N 1/12; C12N 1/14; C12N 1/16; C12N 13/00
See application file for complete search history.

(56) References Cited

U.S. PATENT DOCUMENTS

| | | | |
|---|---|---|---|
| 4,530,360 A | 7/1985 | Duarte | |
| 4,879,011 A | 11/1989 | Schram | |
| 5,554,384 A * | 9/1996 | Samuels et al. ............ | 424/451 |
| 6,835,560 B2 * | 12/2004 | Greene ......................... | 435/167 |
| 8,079,966 B2 | 12/2011 | El-Bialy et al. | |
| 8,292,834 B2 | 10/2012 | El-Bialy et al. | |
| 2003/0153077 A1 * | 8/2003 | Pitt et al. .................... | 435/383 |
| 2004/0191906 A1 | 9/2004 | Holzer | |
| 2004/0197908 A1 | 10/2004 | Ueda et al. | |
| 2006/0106424 A1 | 5/2006 | Bachem | |
| 2007/0020757 A1 | 1/2007 | Zhang et al. | |
| 2007/0082397 A1 | 4/2007 | Hasson et al. | |
| 2007/0249046 A1 | 10/2007 | Shields, Jr. | |
| 2007/0299539 A1 | 12/2007 | Othman et al. | |
| 2008/0021327 A1 | 1/2008 | El-Bialy et al. | |
| 2010/0034735 A1 | 2/2010 | Chen et al. | |
| 2011/0189748 A1 | 8/2011 | Chen et al. | |
| 2011/0275054 A1 | 11/2011 | Chen et al. | |
| 2012/0059287 A1 | 3/2012 | El-Bialy et al. | |
| 2012/0100525 A1 | 4/2012 | Chen et al. | |
| 2012/0135392 A1 | 5/2012 | El-Bialy et al. | |
| 2013/0022957 A1 | 1/2013 | Chen et al. | |
| 2013/0265856 A1 | 10/2013 | Choi et al. | |

FOREIGN PATENT DOCUMENTS

| | | |
|---|---|---|
| EP | 1566201 | 8/2005 |
| WO | 03/089581 | 10/2003 |
| WO | 03089581 | 10/2003 |
| WO | 2008/004752 | 1/2008 |
| WO | 2010/022508 | 3/2010 |
| WO | 2010/022509 | 3/2010 |
| WO | 2013/040688 | 3/2013 |

OTHER PUBLICATIONS

Parvizi, J. et al.; Low-intensity Untrasound Stimulates Proteoglycan Synthesis in Rat Chondrocytes by Increasing Aggrecan Gene Expression; J. Orthop. Res.; 1999; vol. 17; pp. 488-494.

Lin, L. et al.; Ultrasound-Induced Physiological Effects and Secondary Metabolite (Saponin) Production in Panax ginseng Cell Cultures; Ultrasound in Med. & Biol.; 2001; vol. 27, No. 8; pp. 1147-1152.

Yoon, Jong Hyun et al.; Introducing Pulsed Low-Intensity Ultrasound to Culturing Human Umbilical Cord-Derived Mesenchymal Stem Cells; Biotechmol Lett; 2009; vol. 31; pp. 329-335.

Parvizi, J. et al., "Low-intensity ultrasound stimulates proteoglycan synthesis in rat chondrocytes by increasing aggrecan gene expression", Journal of Orthopaedic Research, vol. 17, No. 4, pp. 488-494, (1999).

Lin, L. et al., "Ultrasound-induced physiological effects and secondary metabolite (saponin) production in panax ginseng cell cultures", Ultrasound in Med. & Biology, vol. 27, No. 8, pp. 1147-1152, (2001).

Yoon, J.H. et al., "Introducing pulsed low-intensity ultrasound to culturing human umbilical cord-derived mesenchymal stem cells", Biotechnol Letter, vol. 31, pp. 329-335, (2009).

Chisti, Y. "Sonobioreactors: using ultrasound for enhanced microbial productivity", Trends in Biotechnology, vol. 21, No. 2, pp. 89-93, (2003).

Sontag, W. et al., "Expression of heat shock proteins after ultrasound exposure in HL-60 cells", Ultrasound in Med. & Biol., vol. 35, No. 6, pp. 1032-1041, (2009).

(Continued)

*Primary Examiner* — Ruth Davis
(74) *Attorney, Agent, or Firm* — Evan Law Group LLC

(57) ABSTRACT

A method of increasing the rate of growth, useful product production, or protein expression of a microorganism includes the step of exposing the microorganism to ultrasound having a frequency greater than about 1 MHz.

15 Claims, 8 Drawing Sheets

(56) References Cited

OTHER PUBLICATIONS

Ang, W.T. et al., "Design and implementation of therapeutic ultrasound generating circuit for dental tissue formation and tooth-root healing", IEEE Transactions on Biomedical Circuits and Systems, vol. 4, No. 1, pp. 49-61, (2010).
Bradner, J.R. et al., "Qualitative assessment of hydrolytic activities in antarctic microfungi grown at different temperatures on solid media", World Journal of Microbiology & Biotechnology, vol. 15, pp. 131-132, (1999).
Chen, H. et al., "Key technologies for bioethanol production from lignocelluloses", Biotechnology Advances, vol. 28, No. 5, pp. 556-562, (2010).
Doan, N. et al., "In vitro effects of therapeutic ultrasound on cell proliferation, protein synthesis, and cytokine production by human fibroblasts, osteoblasts, and monocytes", J. Oral Maxillofac Surg., vol. 57, pp. 409-419, (1999).
Khanal, S.K. et al., "Ultrasound enhanced glucose release from corn in ethanol plants", Biotechnology and Bioengineering, vol. 98, No. 5, pp. 978-985, (2007).
Kobayashi, Y. et al., "Low-intensity pulsed ultrasound stimulates cell proliferation, proteoglycan synthesis and expression of growth factor-related genes in human nucleus pulposus cell line", European Cells and Materials, vol. 17, pp. 15-22, (2009).
Leung, K-S. et al., "Complex tibial fracture outcomes following treatment with low-intensity pulsed ultrasound", Ultrasound in Med. & Biology, vol. 30, No. 3, pp. 389-395, (2004).
Min, B-H. et al., "Effects of low-intensity ultrasound (LIUS) stimulation on human cartilage explants", Scand J. Rheumatol., vol. 35, pp. 305-311, (2006).
Osawa, K. et al., "Osteoinduction by microbubble-enhanced transcutaneous sonoporation of human bone morphogenetic protein-2", The Journal of Gene Medicine, vol. 11, pp. 633-641, (2009).
Singhania R.R. et al., "Plant-Based biofuels—An introduction", A. "Handbook of Plant-Based Biofuels", CRC Press, pp. 3-12, (2009).
Rubin, C. et al., "The use of low intensity ultrasound to accelerate the healing of fractures", J. Bone Joint Surg. Am., vol. 83, pp. 259-270, (2001).
Soetaert, W. et al., "Biofuels in Perspective", Biofuels, pp. 1-7, John Wiley & Sons LTD, (2009).
Sun, J-S. et al., "In vitro effects of low-intensity ultrasound stimulation on the bone cells", Journal of Biomedical Materials Research, vol. 57, pp. 449-456, (2001).
Nikolic, S. et al., "Ultrasound-assisted production of bioethanol by simultaneous saccharification and fermentation of corn meal", Food Chemistry, vol. 122, pp. 216-222, (2010).
Teather, R.M. et al., "Use of Congo red-polysaccharide interactions in enumeration and characterization of cellulolytic bacteria from the bovine rumen", Applied and Environmental Microbiology, vol. 43, No. 4, pp. 777-780, (1982).
Wood, B.E. et al., "Ultrasound stimulates ethanol production during the simultaneous saccharification and fermentation of mixed waste office paper", Biotechnol Progress, vol. 13, No. 3, pp. 232-237, (1997).
Yang, F. et al., "Enhancement of enzymatic in situ saccharification of cellulose in aqueous-ionic liquid media by ultrasonic intensification", Carbohydrate Polymers, vol. 81, No. 2, pp. 311-316, (2010).
Zhou, S. et al., "Molecular mechanism of low intensity pulsed ultrasound in human skin fibroblast", J. Biol. Chem., vol. 279, pp. 54463-54469, (2004).
Shaheen, M. et al., "Application of low-intensity pulsed ultrasound to increase bio-ethanol production", Renewable Energy, vol. 57, pp. 462-468, (2013).
Zhao, Y. et al., "Applications of ultrasound to enhance mycophenolic acid production" Ultrasound in Medicine & Biology, vol. 38, issue 9, pp. 1582-1588, (2012).
Radel, S. et al., "Viability of yeast cells in well controlled propagating and standing ultrasonic plane waves", Ultrasonics, vol. 38, pp. 633-637, (2000).

Sainz Herran, N. et al., "Influence of ultrasound amplitude and duty cycle on fungal morphology and broth rheology of *Aspergillus terreus*", World J. Microbiol Biotechnol, vol. 26, pp. 1409-1418, (2010).
Saif Ur Rehman, M. et al., "Use of ultrasound in the production of bioethanol from lignocellulosic biomass", Energy Education Science and Technology Part A: Energy Science and Research, vol. 30, issue 2, pp. 1391-1410, (2013).
Ohgren, K., et al., "High temperature enzymatic prehydrolysis prior to simultaneous saccharification and fermentation of steam pretreated corn stover for ethanol production", Enzyme and Microbial Technology, vol. 40, pp. 607-613, (2007).
Gamauf. C. et al., "Characterization of the bga1-encoded glycoside hydrolase family 35 β-galactosidase of hypocrea jecorina with glacto-β-D-galactanase activity", The FEBS Journal, vol. 274, pp. 1691-1700, (2007).
Xu, P. et al., "Low-intensity pulsed ultrasound-mediated stimulation of hematopoietic stem/progenitor cell viability, proliferation and differentiation in vitro", Biotechnology Letters, vol. 34, issue 10, pp. 1965-1973, (2012).
International Search Report dated Dec. 9, 2009 for PCT application No. PCT/CA2009/001189, 11 pages.
Xie, C.-g. et al., "Marrow mesenchymal stem cells transduced with TPO/FL genes as support for ex vivo expansion of hematopoietic stem/progenitor cells", Cellular and Molecular Life Sciences, vol. 62, pp. 2495-2507, (2005).
Xing, J.Z. et al., "Ultrasound-enhanced monoclonal antibody production", Ultrasound in Medicine and Biology, vol. 38, No. 11, pp. 1949-1957, (2012).
Wofsy, D. et al., "Successful treatment of autoimmunity in NZB/NZW $F_1$ mice with monoclonal antibody to L3T4", Journal of Experimental Medicine, vol. 161, pp. 378-391, (1985).
Yi, H. et al., "Depleting anti-CD4 monoclonal antibody (GK1.5) treatment: influence on regulatory CD4+CD25+Foxp3+ T cells in mice", Transplantation, vol. 85, No. 8, pp. 1167-1174, (2008).
Markvicheva, E. et al., "The effect of low-intensity ultrasound on hybridoma cell proliferation and monoclonal antibody production in hollow fiber bioreactor", European Journal of Cell Biology, vol. 69, No. suppl. 42, #465, p. 155, Conference Abstract from the $21^{st}$ Annual Meeting of the German Society for Cell Biology, Hamburg, Germany, Mar. 24-28, 1996.
Lv, Y. et al., "Effects of low-intensity pulsed ultrasound on cell viability, proliferation and neural differentiation of induced pluripotent stem cells-derived neural crest stem cells", Biotechnology Letters, vol. 35, issue 12, pp. 2201-2212, (2013).
International Search Report dated Dec. 10, 2009, for PCT application No. PCT/CA2009/001188, 11 pages.
Bensinger, W. et al., "Improving stem cell mobilization strategies: future directions", Bone Marrow Transplantation, vol. 43, pp. 181-195, (2009).
Birch, J.R. et al., "Antibody production", Advanced Drug Delivery Reviews, vol. 58, pp. 671-685, (2006).
Bordignon, C. "Stem-cell therapies for blood diseases", Nature, vol. 441, pp. 1100-1102, (2006).
Brada, S. et al., "The supportive effects of erythropoietin and mast cell growth factor on CD34+/CD36-sorted bone marrow cells of myelodysplasia patients", Blood, vol. 88, pp. 505-510, (1996).
Brada, S.J.L. et al., "Characterization of the erythropoiesis in myelodysplasia by means of ferrokinetic studies, in vitro erythroid colony formation and soluble transferrin receptor", Leukemia, vol. 12, pp. 340-345, (1998).
Bradley, M.B. et al., "Cord blood immunology and stem cell transplantation", Human Immunology, vol. 66, pp. 431-446, (2005).
Brugger, W. et al., "Reconstitution of hematopoiesis after high-dose chemotherapy by autologous progenitor cells generated ex vivo", The New England Journal of Medicine, vol. 333, No. 5, pp. 283-287, (1995).
Choi, W.H. et al., "Low-intensity ultrasound increased colony forming unit-fibroblasts of mesenchymal stem cells during primary culture", Tissue Engineering: Part C, vol. 17, No. 5, pp. 517-526, (2011).
Conneally, E. et al., "Expansion in vitro of transplantable human cord blood stem cells demonstrated using a quantitative assay of their lympho-myeloid repopulating activity in nonobese diabetic-scid/scid

(56) References Cited

OTHER PUBLICATIONS mice", Proceedings of the National Academy of Sciences of the United States of America, vol. 94, pp. 9836-9841, (1997).

Copelan, E.A. "Hematopoietic stem-cell transplantation", The New England Journal of Medicine, vol. 354, No. 17, pp. 1813-1826, (2006).

Dahlberg, A. et al., "Ex vivo expansion of human hematopoietic stem and progenitor cells", Blood, vol. 117, No. 23, pp. 6083-6090, (2011).

El-Bialy, T. "Therapeutic ultrasound applications in craniofacial growth, healing and tissue engineering", Rejuvenation Research, vol. 10, No. 3, pp. 367-371, (2007).

Gluckman, E. "Ten years of cord blood transplantation: from bench to bedside", British Journal of Haematology, vol. 147, pp. 192-199, (2009).

Guilak, F. et al., "Control of stem cell fate by physical interactions with the extracellular matrix", Cell Stem Cell, vol. 5, pp. 17-26, (2009).

Gul, H. et al., "Valproic acid increases CXCR4 expression in hematopoietic stem/progenitor cells by chromatin remodeling", Stem Cells and Development, vol. 18, No. 6, pp. 831-838, (2009).

Gul, H. et al., "Magnetic carbon nanotube labelling for haematopoietic stem/progenitor cell tracking", Nanotechnology, vol. 21, pp. 1-9, (2010).

Harris, G.R., "Progress in medical ultrasound exposimetry", IEEE Transactions on Ultrasonics, Ferroelectrics, and Frequency Control, vol. 52, No. 5, pp. 717-736, (2005).

Heckman, J.D. et al., "Acceleration of tibial fracture-healing by non-invasive, low-intensity pulsed ultrasound", The Journal of Bone & Joint Surgery, vol. 76-A, No. 1, pp. 26-34, (1994).

Iwashina, T. et al., "Low-intensity pulsed ultrasound stimulates cell proliferation and proteoglycan production in rabbit intervertebral disc cells cultured in alginate", Biomaterials, vol. 27, pp. 354-361, (2006).

Kaufmann, H. et al., "Metabolic engineering of mammalian cells for higher protein yield", Gene Transfer and Expression in Mammalian Cells, Chapter 15, pp. 457-469, (2003).

Kaushansky, K. "Thrombopoietin and the hematopoietic stem cell", Blood, vol. 92, No. 1, pp. 1-3, (1998).

McNiece, I. et al., "Ex vivo expanded peripheral blood progenitor cells provide rapid neutrophil recovery after high-dose chemotherapy in patients with breast cancer", Blood, vol. 96, No. 9, pp. 3001-3007, (2000).

Mottram, P.L. et al., "Transgenic anti-CD4 monoclonal antibody secretion by mouse segmental pancreas allografts promotes long term survival", Transplant Immunology, vol. 8, pp. 203-209, (2000).

Petzer, A.L. et al., "Differential cytokine effects on primitive (CD34+ CD38−) human hematopoietic cells: novel responses to Flt3-ligand and thrombopoietin", The Journal of Experimental Medicine, vol. 183, pp. 2551-2558, (1996).

Praloran, V. et al.,"Blood erythroid progenitors (CFU-E and BFU-E) in acute lymphoblastic leukemias", Blut, vol. 58, pp. 75-78, (1989).

Qiu, Y. et al., "The correlation between acoustic cavitation and sonoporation involved in ultrasound-mediated DNA transfection with polyethylenimine (PEI) in vitro", Journal of Controlled Release, vol. 145, pp. 40-48, (2010).

Rodrigues, M.E. et al., "Technological progresses in monoclonal antibody production systems", Biotechnology Progress, vol. 26, No. 2, pp. 332-351, (2010).

Rubinstein, P. "Why cord blood?", Human Immunology, vol. 67, pp. 398-404, (2006).

Scheven, B.A.A. et al., "Therapeutic ultrasound for dental tissue repair", Medical Hypotheses, vol. 73, pp. 591-593, (2009).

Shah, A.J. et al., "Flt3 ligand induces proliferation of quiescent human bone marrow $CD34^+CD38$ cells and maintains progenitor cells in vitro", Blood, vol. 87, No. 9, pp. 3563-3570, (1996).

Sriram, S. et al., "In vivo immunomodulation by monoclonal anti-CD4 antibody II. Effect on T cell response to myelin basic protein and experimental allergic encephalomyelitis", The Journal of Immunology, vol. 141, No. 2, pp. 464-468, (1988).

Doherty, T.A. et al., "CD4+ cells are required for chronic eosinophilic lung inflammation but not airway remodeling", American Journal of Physiology—Lung Cellular and Molecular Physiology, vol. 296, pp. L229-L235, (2009).

Villaron, E.M. et al., "In leukapheresis products from non-Hodgkin's lymphoma patients, the immature hematopoietic progenitors show higher CD90 and CD34 antigenic expression", Transfusion and Apheresis Science, vol. 37, pp. 145-156, (2007).

Wurm, F.M. "Production of recombinant protein therapeutics in cultivated mammalian cells", Nature Biotechnology, vol. 22, No. 11, pp. 1393-1398, (2004).

Zhang, Z-J. et al., "The effects of pulsed low-intensity ultrasound on chondrocyte viability, proliferation, gene expression and matrix production", Ultrasound in Medicine & Biology, vol. 29, No. 11, pp. 1645-1651, (2003).

Ziskin, M.C., "Applications of ultrasound in medicine—comparison with other modalities", Ultrasound: Medical Applications, Biological Effects, and Hazard Potential, pp. 49-59, (1987).

International Search Report and Written Opinion dated Jan. 11, 2013, for PCT application No. PCT/CA2012/000873, 14 pages.

Regueira, T.B. et al., "Molecular basis for mycophenolic acid biosynthesis in *Penicillium brevicompactum*", Applied and Environmental Microbiology, vol. 77, No. 9, pp. 3035-3043, (2011).

Takagi, M. "Cell processing engineering for ex-vivo expansion of hematopoietic cells", Journal of Bioscience and Bioengineering, vol. 99, No. 3, pp. 189-196, (2005).

Barnett, S.B. et al., "Is pulsed ultrasound mutagenic?", Ultrasound Med. Biol., Supplemental 2, pp. 45-48, (1983).

Pui, P.W.S. et al., "Batch and semicontinuous aggregation and sedimentation of hybridoma cells by acoustic resonance fields", Biotechnology Prog., vol. 11, No. 2, pp. 146-152, (1995).

Gul-Uludag, H. et al., "Abstract of Ultrasound stimulation enhances proliferation of hematopoietic stem/progenitor cells: Implications for clinical transplantation, gene and cellular therapies", Annual Conference of International Society for Cellular Therapy, Philadelphia, PA, May 25, Cytotherapy, 12:40, (2010).

Sontag, Wetner et al., "Expression of Heat Shock Proteins After Ultrasound Exposure In HL-60 Cells", Ultrasound in Med. & Biol. vol. 35, No. 6, pp. 1032-1041, 2009.

El-Bialy, T. et al., "Cell expansion genes expression by therapeutic ultrasound. Pros and cons", Canadian Accoustics, vol. 36, No. 3, pp. 40-41, (2008).

Ang, W. T. et al., "System-on-chip ultrasonic transducer for dental tissue formation and stem cell growth and differentiation", Proceedings of the IEEE Symposium on Circuits and Systems, Seattle, pp. 1818-1821, (May 2008).

Brian997, "Stem cells", found at http://hronrad.wordpress.com/2013/12/05/stem-cells/, pp. 1-3, May 12, 2013.

* cited by examiner (a) The plate made of ultrasound transducer array (b) The liquid within the bottom on top of the plate will receive even ultrasound treatment

ULTRASOUND ENHANCED GROWTH OF MICROORGANISMS

CROSS REFERENCE TO RELATED APPLICATIONS

This application is a Continuation-In-Part application of co-pending U.S. patent application Ser. No. 13/060,860 filed Aug. 26, 2009, which is a US National Phase Application under 35 U.S.C. §371 of International Application No. PCT/CA2009/001189 filed Aug. 26, 2009, designating the US and claiming priority from U.S. Provisional Application No. 61/091,830 filed Aug. 26, 2008.

FIELD OF THE INVENTION

The invention relates to methods of increasing the rate of growth, useful product production, or protein expression of a microorganism by exposing the microorganism to low intensity pulsed ultrasound (LIPUS) stimulation.

BACKGROUND OF THE INVENTION

Cell cultures are used widely in science and industry for purposes varying from protein production, food and beverage fermentation to pharmaceutical production. Cell cultures are often used in laboratory settings for research and disease diagnosis and, with the advent of genetic engineering, modified organisms are commonly used for the production of medical proteins, antibiotics, cytokines, insulin, hormones, and other biomedically-important molecules.

Fermentation is one of the most important processes in the pharmaceutical industry. Industrial fermentation loosely refers to the breakdown of organic substances and re-assembly into other substances. Fermenter culture in industrial capacity often refers to highly oxygenated and aerobic growth conditions. For instance, penicillin, which brought enormous profits and public expectations, was produced industrially using a deep fermentation process. When a particular organism is introduced into a selected growth medium, the medium is inoculated with the particular organism. Growth of the inoculums does not occur immediately, but follows a lag phase. Subsequently the rate of growth of the organism steadily increases, for a certain period known as the log or exponential phase. The rate of growth eventually slows down due to the continuously falling concentrations of nutrients and the continuously increasing (accumulating) concentrations of toxic substances. This phase, where the increase of the rate of growth is checked, is the deceleration phase. After the deceleration phase, growth ceases and the culture enters a stationary phase or steady state.

The fermentation industry relies on bacterial and fungal cultures to produce alcoholic beverages, process a wide variety of foods, neutralize toxic spills, break down liquid and solid wastes, create biologically-significant compounds, and transform corn and other raw materials into bio-fuels such as bio-ethanol. Bio-ethanol is a biodegradable, non-toxic renewable energy source which is expected to contribute significantly to solving the world's energy crisis (Soetaert and Vandamme, 2009). Bio-ethanol is produced mainly from agricultural products and food wastes containing sugar, starch, or cellulose which can be fermented and distilled into ethanol. However, the conversion of sugar or starch to bio-ethanol requires large areas of land to grow raw materials, and may negatively impact the food industry by removing available food (Pandey, 2008). Lignocellulosic ethanol can be produced from a variety of unutilized feedstock, with typical sources of lignocellulosic biomass including bugasse of sugar cane, corn stover, grasses, woody biomass, industrial wastes, and dedicated woody crops (Pandey, 2008). Due to the high crystallinity of lignocelluloses, it is unfortunately difficult to hydrolyze into individual glucose subunits for fermentation and the cost of cellulase enzymes required for hydrolysis can account for 30-50% of the total operation costs (Chen and Qiu, 2010; Yang et al., 2010).

In almost all useful applications of cell cultures, the rate at which the desired product is produced is limited only by the rate at which protein expression occurs, and the growth rate of the cells used in production. Industrial fermentation most often takes place in a specially designed environment in which cells are grown in suspension. The fermenter maximizes cell growth by carefully maintaining optimal temperature and agitating the contained mixture to ensure transfer of nutrients into and metabolic byproducts out of the cell. However, it is difficult to ensure that the turbulence in the tank is pervasive enough to affect the cells on the microscopic level. There is often a relatively stagnant region directly adjacent to the walls of the cells and the fermenter itself. This naturally has a negative effect on the nutrient and toxin transfer to and from the cells, and reduces the rate of protein expression, lowering the overall productivity of the fermentation process.

As fermentation is a widely practiced art and has many industrial applications, it is clear that some method of improving the rate of cell protein expression, ethanol, and biodrugs production would be desirable.

Ultrasound is broadly defined as sound waves at a frequency above the normal hearing range, or a frequency greater than 20 kHz (Khanal et al., 2007). Ultrasound is traditionally used in medical diagnosis, such as fetal imaging, which employs frequencies between 2 MHz and 18 MHz and therapeutic treatment of injured muscles, ligaments and tendons, using frequencies between 1 to 5 MHz.

Ultrasonic stimulation creates "microcavitation" or the creation of minute bubbles in a liquid known as "microcavities." With each sound wave, these bubbles expand and contract, creating tremendous force and turbulence on a microscopic scale. In some cases, this sound wave is powerful enough to collapse the cavities, which causes even more extreme turbulence, high temperatures, and free radicals in the vicinity of the former cavity. These collapses are powerful enough to dislodge or even destroy cells.

Ultrasonic applications rely on these processes. One common use of ultrasound is as an effective cleaning agent. If the intensity is high enough, collapse cavitation is the dominant factor in the cells' environment. This can strip or even kill harmful bacteria from a surface. The effectiveness of this technique has been proven by applying ultrasound to one end of a glass tube using frequencies around 100 kHz and intensities around 40 W/cm$^2$. It was found that approximately 88% of the bacteria were removed from the surface of the tube. Similar experiments have been carried out in a variety of situations, including stripping biofilms from reverse osmosis membranes. Ultrasound is now actively sold to laboratories as a cleaning aid.

As well as dislodging bacteria, very high intensity ultrasound (>10 W/cm$^2$) has been used to kill suspended bacteria. This relies on collapse cavitation to rend the bacterial membrane.

Applications also exist for low intensity pulsed ultrasound (LIPUS) which generally utilizes an intensity of about 0.1-0.2 W/cm$^2$. LIPUS has been used for repair of bone fractures (Rubin et al., 2001), cell stimulation and differentiation (Yoon et al., 2009), stimulation of growth factors (Kobayashi et al., 2009), protein and fibroblast growth (Doan et al., 1999;

Min et al., 2006; Sun et al., 2001; Wood et al., 1997; Zhou et al., 2004), dental tissue formation (Ang et al., 2010; Leung et al., 2004), stem cell proliferation (Gul et al., 2010), sonoporation including ultrasound-mediated gene delivery (Osawa et al., 2009), and biomass pre-treatment before saccharification (Svetlana et al., 2010). It is believed that ultrasonic waves can improve the rate of bone growth and indeed, almost 80% of North American physiotherapists possess ultrasonic emitters for the purpose of encouraging speedy recovery. However, only LIPUS is effective in this situation, with LIPUS devices being currently being marketed for this purpose (see for example, U.S. Pat. No. 4,530,360 to Duarte).

Use of low-intensity pulsed ultrasound to aid the healing of flesh wounds is described, for example, in U.S. Patent Application Publication No. 2006/0106424 A1 to Bachem. The method utilizes ultrasound to increase the phagocytic action of the human body's macrophages. However, the method provides no solution for the use of ultrasound outside the confines of a wound.

U.S. Patent Application Publication No. 2003/0153077 A1 to Pitt et al. describes a method in which low-intensity ultrasound can stimulate the growth of biofilms and other cells. By balancing the beneficial turbulence produced by collapse cavitation with its accompanying negative effects, it was found that low-intensity ultrasound can improve growth rates of cells by up to 50%. The experimenters tested their findings on human and bacterial cells, using frequencies from about 20 kHz to about 1 MHz and intensities encompassing the range from 1 to 5000 mW/cm$^2$. Unfortunately, though increased cell growth is beneficial to the fermentation process, the parameters investigated by this group do not provide the optimal rate of protein expression in fermentation processes.

SUMMARY OF THE INVENTION

The present invention provides methods of increasing the rate of growth of microorganisms, useful enhance production of useful products, and/or protein expression in microbial cells by stimulation with calibrated ultrasound. The increased growth, enhanced production, and/or protein expression may take place in the context of a useful process, such as fermentation anaerobic digestion or bioremediation, for example.

In one aspect, the invention comprises a method of enhancing the rate of cell growth, useful product production, and/or protein expression in a cell culture through exposure to ultrasound of specified frequencies and intensities. These methods are beneficial to cells in the vast majority of environments, creating turbulence on the microscopic scale in the area immediately adjacent to the walls of the cells and other solid surfaces.

The ultrasound may have a frequency between about 1 MHz to about 10 MHz, and preferably between about 1 MHz to about 2 MHz, depending inter alia on the species of cell used in culture. In one embodiment, the ultrasound has a frequency between about 1.4 MHz to about 1.6 MHz. In one embodiment, it consists of a pulsed ultrasound, which assists in minimizing temperature increase of the environment. In one embodiment, pulses generated at a duty cycle of approximately 4:1 (off:on), with a pulse period of approximately 1 second, are effective. In one embodiment, the ultrasound is calibrated to achieve a balance of the harmful effects of "collapse cavitations" caused by the ultrasound and the beneficial turbulence it affords the cells, allowing increased nutrient uptake and metabolic byproduct expulsion.

In one aspect of the invention, there is also a method of sensing the intensity of the ultrasonic waves employed, as "felt" by the target cells. This is not, however, necessary in all circumstances, and the method can proceed without such detection. The measurement can be taken with any ultrasound-measuring device operatively connected to the ultrasound emitter. In one embodiment, the method further comprises the step of relaying collected information back to the ultrasonic emitter if said sensor is employed. This may be through a wired or wireless connection.

In another aspect, the invention comprises a method of correcting the emitted output to maximize the effectiveness of the ultrasound, based on the sensed intensities, if said sensor is employed. This assists in maximizing protein expression.

The target cells may be eukaryotic or prokaryotic, and may comprise fungal or bacterial cells. The cells may be natural or modified.

The ultrasound may have an intensity greater than about 10 mW/cm$^2$ up to about 5000 mW/cm$^2$, depending on the fragility of the cells in culture.

In one embodiment, the ultrasound can be directed such that reflections and interference are minimized, or tuned to give maximum effectiveness to the ultrasonic emission.

In one embodiment, the ultrasonic emitter may be placed inside a fermenter, or attached to a solid emitting surface outside a fermenter, or other suitable configurations.

In situations of fermentation that do not occur in a fermenter or digestion, the method may still be applied, with the ultrasound emitted to have maximum coverage of the cells whose protein expression is desired to be enhanced. In such cases, for example, in situ bacterial bioremediation, ultrasound emitters may be strategically placed, and may be moved periodically.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order that the above-recited and other features and advantages of the present invention will be readily understood, a more particular description of the invention is given. A specific example thereof is detailed, the result of which are illustrated in the appended figures. The following example is only a single embodiment of the invention, and is not to be considered in any way the limit of its scope. In the accompanying figures.

Control, or 844 CK) after three days. 844 A2, 844 C2 and 844 E2 represent different LIPUS intensities, namely 10 mW/cm$^2$, 50 mW/cm$^2$ and 100 mW/cm$^2$, respectively. This illustrates the effectiveness of LIPUS, as well as its reliance on specific properties of the ultrasound, such as intensity and frequency. Ultrasound of too high an intensity can actually hinder growth.

Figure 4:
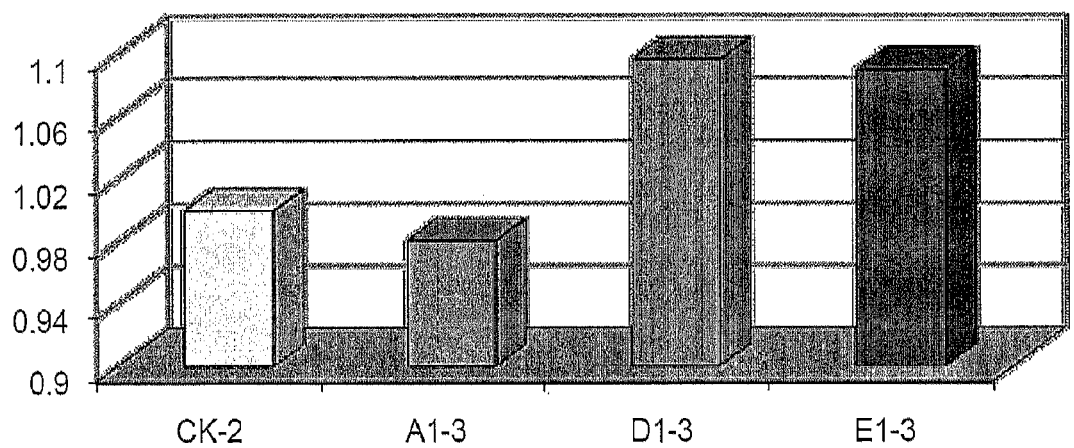

FIG. 4 shows biomass comparison after ultrasound treatment (mg) of different intensities: CK-2 is the control; A1-3 is 80 mW/cm$^2$; D1-3 is 60 mW/cm$^2$; and E1-3 is 30 mW/cm$^2$.

Figure 5:
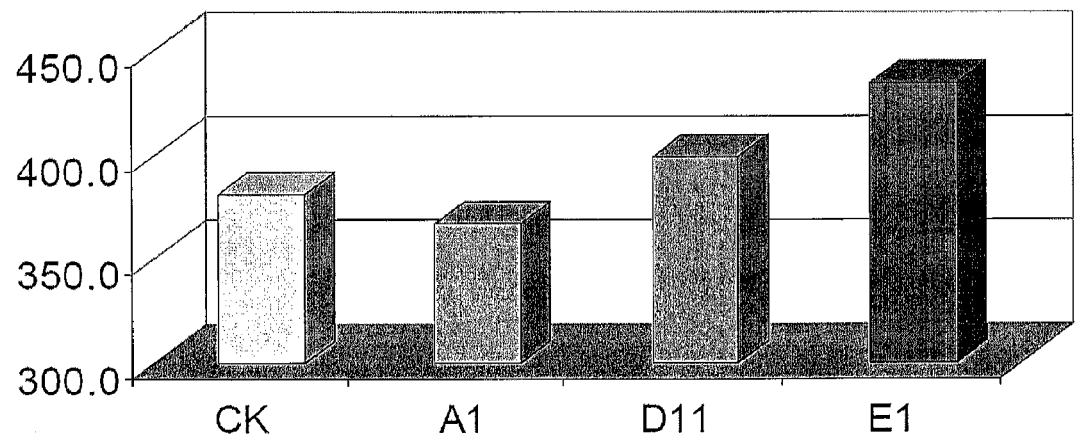

FIG. 5 shows the concentration (μg/ml) of a fermentation product (mycophenolic acid) after ultrasound treatment of different intensities (same as shown in FIG. 4) compared to a control.

Figure 6:
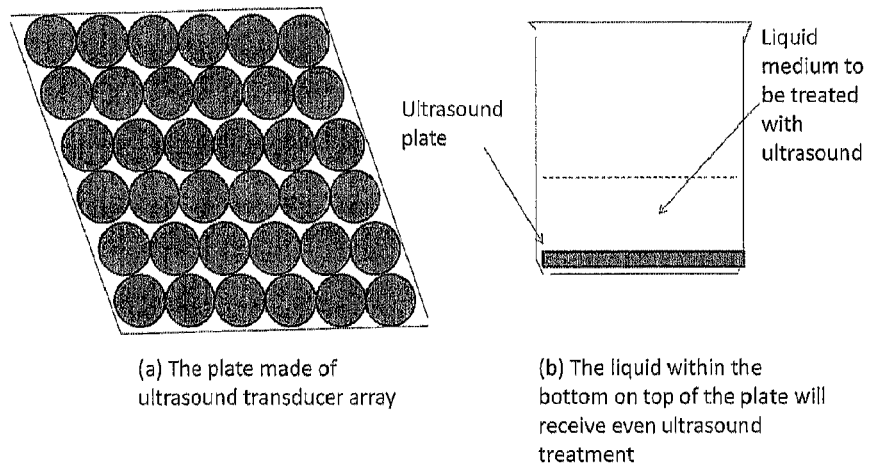

FIG. 6 shows one embodiment of an ultrasound transducer array for use in larger volume liquid culture.

Figure 7:
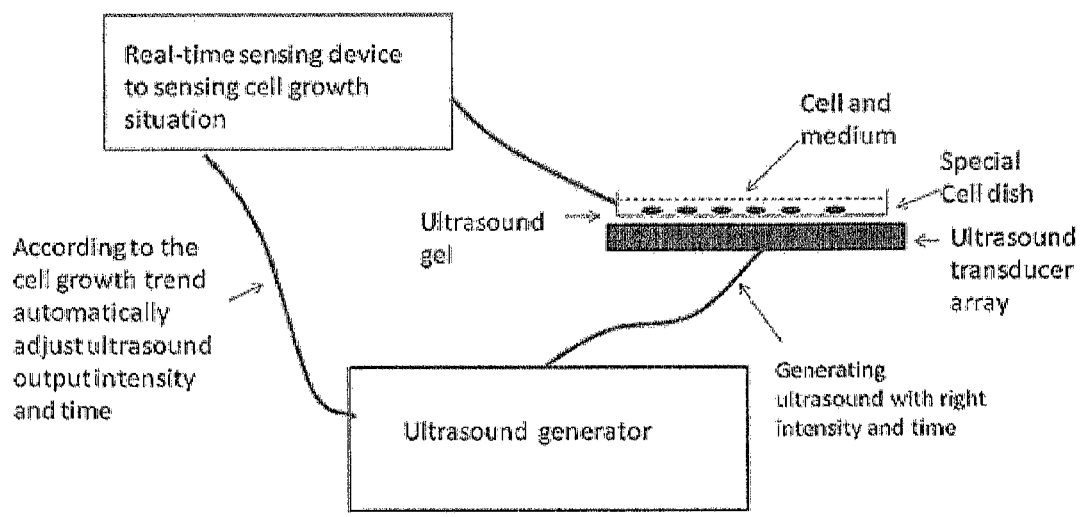

FIG. 7 is a schematic representation of an ultrasound system employing system feedback.

Figure 8:
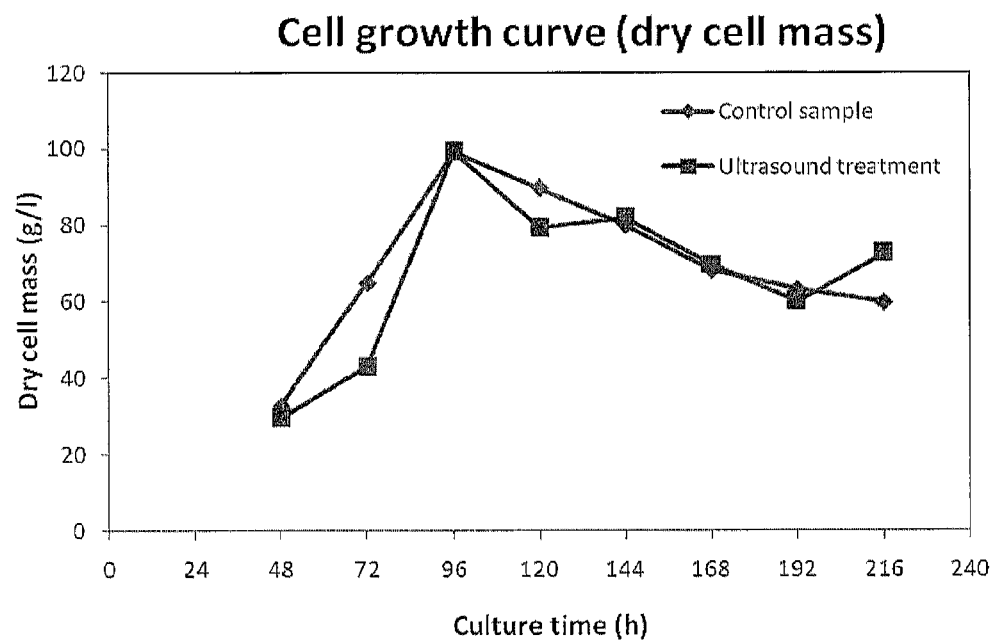

FIG. 8 is a graph comparing the cell growth curves over time for cultures treated with or without ultrasound.

Figure 9:
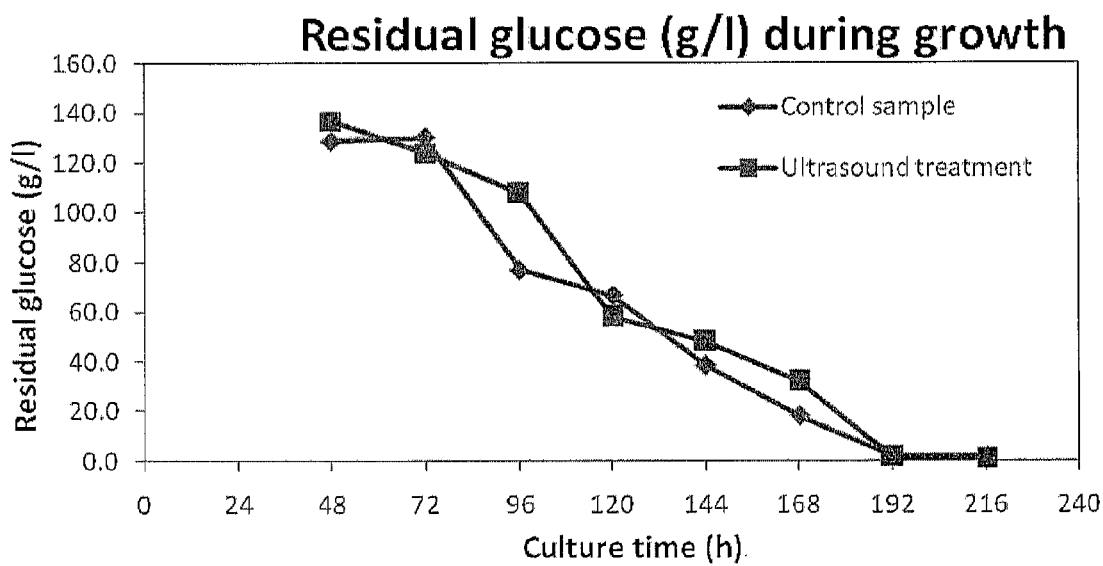

FIG. 9 is a graph comparing residual glucose over time for cultures treated with or without ultrasound.

Figure 10:
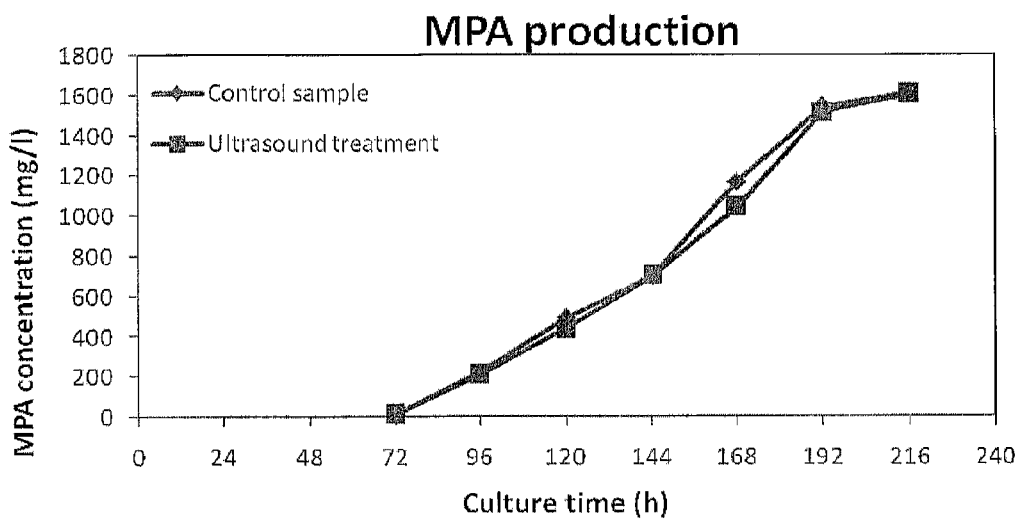

FIG. 10 is a graph comparing the production of MPA over time by cultures treated with or without ultrasound.

Figure 11:
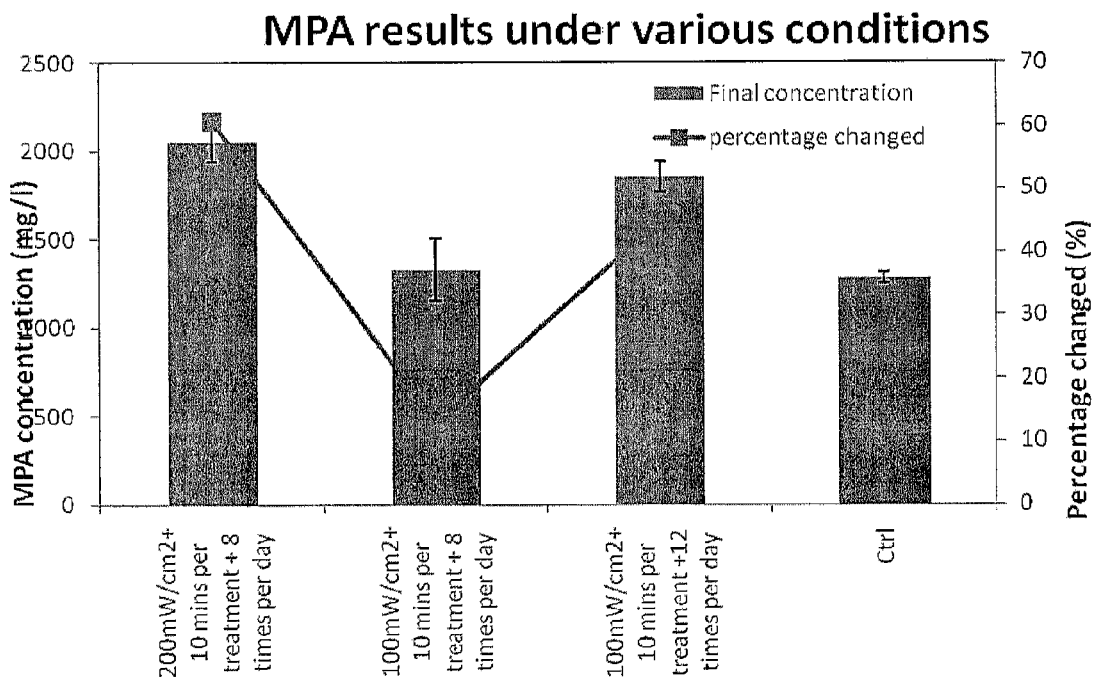

FIG. 11 is a graph comparing MPA production under various ultrasound conditions.

Figure 12:
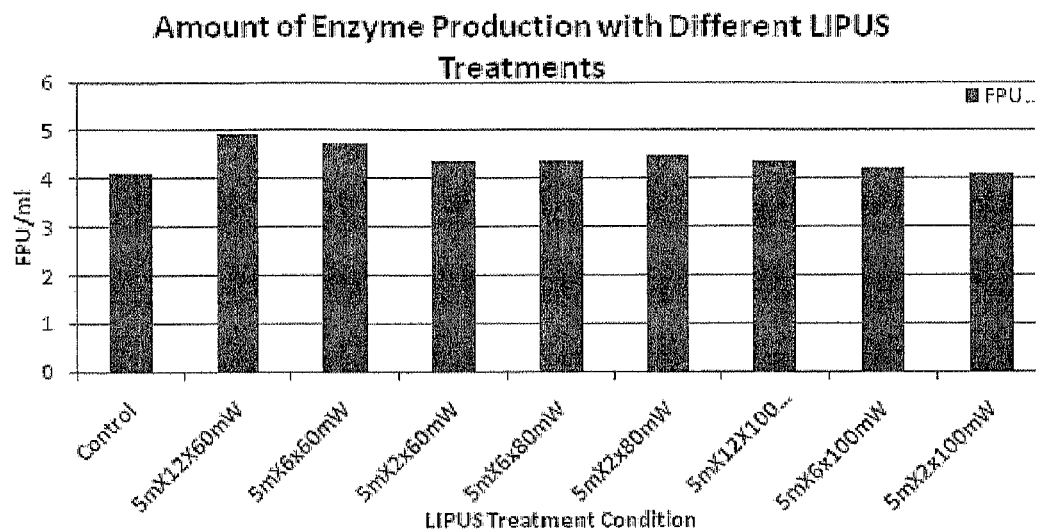

FIG. 12 is a graph showing cellulase activity (FPU/ml) of five-day old culture supernatants treated with different LIPUS conditions during fermentation ("5 m×12×60 mW" refers to 5 minutes exposure time, 12 times a day at two hour intervals with a LIPUS power of 60 mW/cm$^2$).

Figure 13:
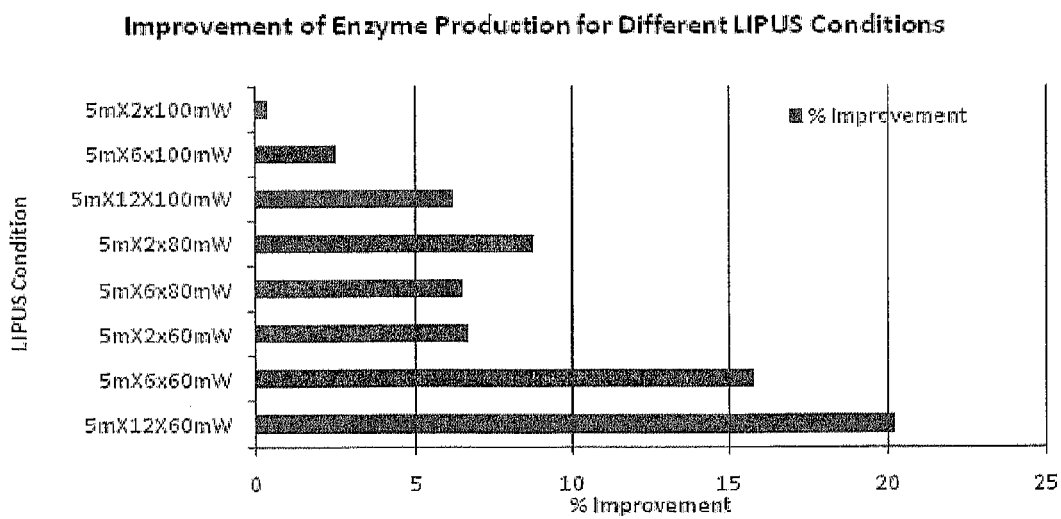

FIG. 13 is a graph showing the improvement of cellulase production as determined by cellulase activity (FPU/ml) in cultures which received different LIPUS treatment during fermentation compared to untreated samples.

Figure 14:
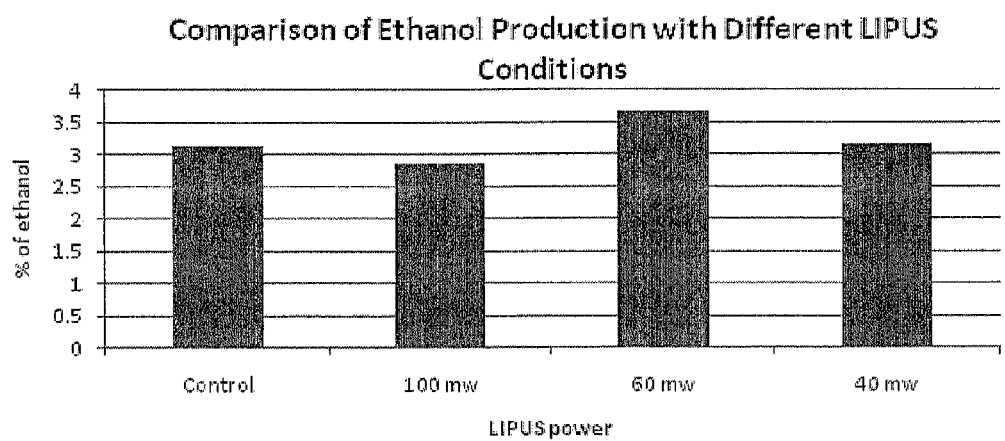

FIG. 14 is a graph showing the ethanol concentration (%) in five-day old cultures treated with different LIPUS conditions during fermentation.

Figure 15:
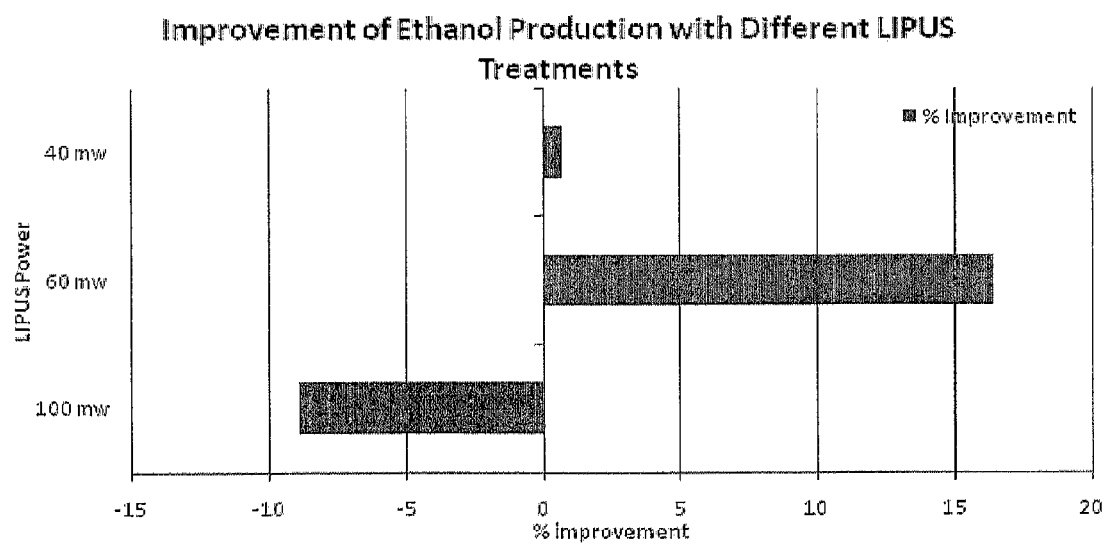

FIG. 15 is a graph showing the improvement in ethanol production for cultures which received different LIPUS treatment during fermentation compared to untreated samples.

DETAILED DESCRIPTION OF PREFERRED EMBODIMENTS

Embodiments of the invention may be understood by referring to the following description and drawings. The methods of the present invention, as generally described herein, can be practiced and varied in many ways. Thus, the following more detailed description of the methods of the present invention is not intended to limit the scope of the invention as claimed. Instead, the detailed description is merely representative of the presently considered embodiments.

As used herein, the term "microorganism" includes prokaryotic organisms and unicellular eukaryotic organisms. Microorganisms may include, without limitation, bacteria, fungi, archaea, and protists. Microorganisms include unicellular organisms which may be used in industrially useful processes, such as fermentation, bioremediation or production of bioproducts.

As used herein, the term "fungus" or "fungi" is used to mean a member of the kingdom Fungi which includes the phyla Ascomycota (for example, *Trichoderma* species, and yeasts including *Saccharomyces* species), Basidiomycota (club fungi, mushrooms), Zygomycota (bread molds), Oomycota (water molds) and Deuteromycota (for example, *Penicillium* species).

As used herein, the term "fermentation" is broadly used to mean the bulk growth of microorganisms on or in some growth medium. No distinction is made between aerobic and anaerobic metabolism when the word is used in this sense. Anaerobic fermentation is the energy-yielding anaerobic metabolic breakdown of a nutrient molecule, such as glucose, without net oxidation. Fermentation may typically yield lactate, acetic acid, ethanol, or some other simple product.

The present invention comprises the application of high-frequency ultrasound to microorganisms to enhance their growth, useful product production, and/or protein expression. The subject microorganisms may exist in liquid or solid culture, or may exist in uncontrolled environments. The useful products produced by microorganisms subjected to a method of the present invention may include gases, oils, organic acids, alcohols or proteins. In one embodiment, the microorganisms may be involved in breaking down or digesting a substrate, such as in an anaerobic digester or a bioremediation process.

It is not known with certainty why ultrasound applied in accordance with the present invention enhances cell growth, useful product production, and/or protein expression. Without being limited to any one theory, it appears that the present invention increases cell growth, useful product production, and/or protein expression by allowing more rapid transport of essential materials into the cell, and allowing quicker dispersion of metabolic by-products away from the cell.

Though most fermentation tanks already address this problem by stirring or shaking the cell cultures inside of them, it is theorized that a microscopic buffer remains around solid surfaces or cell walls in which fluid movement is greatly constrained. If the fluid immersing the cell is stagnant in the area directly adjacent to the cell, it is not conducive to the transport of small molecules (such as oxygen, amino acids, carbon dioxide or other gases) away from or towards the cell.

A liquid surrounding a cell culture contains bubbles of gas which compress and relax, causing them to contract and expand, when exposed to ultrasound. This movement creates resultant forces on the liquid surrounding the gas bubbles. When the bubble is compressed, liquid is "pulled" into the area around the now smaller bubble, and when the bubble expands, liquid is pushed away. This causes considerable turbulence on the microscopic level. This turbulence is even slightly topical, as gas bubbles will preferentially form near cell walls or solid surfaces, precisely the original locations of the stagnancy.

If the pressures are high enough (this is caused by ultrasound of a high intensity), bubbles can collapse down to nothing. Simple thermodynamics will demonstrate that the temperature will rise precipitously in such an incidence (one study claims temperatures as high as 5000 K), and the collapse results in a shock wave of heat and "shear force," or force directed towards the bubble's center. The collapse produces turbulence on a massive scale, allowing even faster transfer of nutrients and wastes. However, at the same time, the heat and force may be intense enough to damage or tear open the cell wall itself. The intensity and frequency of ultrasound in this invention must be able to afford a balance between the harmful and beneficial effects of the cavitations.

The present invention is intended to aid cell growth, useful product production, and/or protein expression by increasing the transfer of substances in the vicinity of the cellular membranes. Enhanced cell growth and protein expression are usually positively co-related, and enhancement of one will typically result in, or be caused by, enhancement of the other.

*T. reesei* is the fungus variety that is used in the creation of almost all biofuels, including conventional ethanol, butanol, and cellulosic ethanol. The latter product is an efficient and relatively inexpensive biofuel that can be made from organic waste and other inedible plant matter. Cellulosic ethanol especially is hailed as the future alternative to fossil fuels, and the commercialization of its production is already beginning. One major hurdle to this commercialization, however, is the almost prohibitive cost and the immense time involved in its production. Optimizing *T. reesei* will allow butanol producers to increase the rate at which the *T. reesei* cells undergo protein expression, and thus increase the output of butanol.

Cellulosic ethanol is produced from the non-food portions of crops, such as straw and other organic wastes. Though this is greatly preferred to using edible materials to produce fuels, it again is a more costly and time-intensive process, and embodiments of the present invention could increase the rate at which cellulosic ethanol can be produced.

Mycophenolic acid (MPA) is an antibiotic and immune-suppressive agent which has many specific effects for human cells. It is a secondary metabolite and is generally produced through fermentations by several species of *Penicillium*. The present invention may be applied to increase fermentation-based drug production. In one embodiment, low-intensity pulsed ultrasound is used to enhance *Penicillium brevicompactum* fermentation for the production of MPA.

High frequency ultrasound (greater than about 1 MHz) may be applied in many different contexts to enhance cell growth, useful product production, and/or protein expression in a cell culture. Such potential applications include increased protein expression in laboratory cultures, allowing faster tests and diagnoses, faster production of pharmaceuticals, growth hormones, regulatory factors, proteins, and a wide array of other biomedical substances.

The biocultures of yeasts, bacteria, fungi, and other such microorganisms that transform chemical substances represents another possible implementation of the technology, including implementations not specifically mentioned above. In one embodiment, low-intensity pulsed ultrasound is used to enhance *Saccharomyces cerevisiae* fermentation of sugars for the production of ethanol.

We have found that ultrasound has beneficial effects on cell growth in microbial cell culture when applied at a high frequency, greater than about 1 MHz. Prior art use of ultrasound stimulation involved frequencies in the range of 20 kHz to 1 MHz. We have surprisingly found that that the optimal frequency in many cases was higher than 1 MHz. Thus, in one embodiment, the ultrasound frequency is greater than about 1 MHz, and less than about 2 MHz. Around 1.5 MHz, tests revealed that many cell types, including stem cells and other animal cells, were allowed maximum "micro-agitation" while only sustaining minimal damages to cellular structure. Therefore, in one embodiment, the ultrasound is greater than about 1.4 MHz, and less than about 1.6 MHz. In one preferred embodiment, 1.4 MHz and about 1.6 MHz were found to be particularly useful when applied to *T. reesei*.

Possible applications also exist for employing the technology in non-cultured examples; that is, cells that are not in specifically controlled environments. Though such environments were the locations of microbial cell culture in a laboratory setting, embodiments of the present invention may also be applied in a less controlled situation, such as bioremediation in the environment, or large scale anaerobic digesters.

Different cells have different strengths and weaknesses, and all cells may not require the same frequencies and intensities. These differences are predicted to be greatest between the classes of microorganisms, prokaryotes and eukaryotes. The method herein provides the windows of frequencies and intensities that allow for optimal performance among these different varieties of cells.

The intensity of the ultrasound energy may be greater than about 5 mW/cm$^2$ up to about 5000 mW/cm$^2$. In one embodiment, the intensity is preferably between about 40 mW/cm$^2$ and about 80 mW/cm$^2$, and in one embodiment, an optimal intensity was about 60 mW/cm$^2$.

In one embodiment, the cells in question are subjected to ultrasonic stimulation from an ultrasonic emitter placed near enough to the target area to deliver waves of a specific frequency and intensity, which will be discussed below. In one embodiment, the ultrasound is applied during logarithmic growth phase of a cell culture; however, its beneficial effects may be realized during any growth phase. Sustained stimulation with ultrasound is not necessary. Increased growth rate or protein expression may be obtained by applying ultrasound in intervals less than one hour per 24 hour period. In one embodiment, stimulation intervals of only between about 10 minutes and 20 minutes per 24 hour period is all that is required to reap benefits of ultrasound application.

Optimization of a suitable frequency and intensity for any given microbe and growth condition may be determined by empirical study, without undue experimentation, by those skilled in the art. In general, however, prokaryotic cells are naturally more durable than eukaryotic cells and thus can withstand a higher intensity ultrasonic stimulation. Intensity ranges have been briefly discussed in Pitt et al. (2003) which places the approximate intensity ranges for eukaryotic cells at 8-50 mW/cm$^2$ and for prokaryotic cells at 2-2.2 W/cm$^2$. All trials conducted by Pitt et al. used a frequency of 70 kHz.

In one embodiment, the ultrasound is pulsed, as prolonged exposure can cause heat buildup and damage the treated cells. The duration and timing of the pulses may again be chosen by one skilled in the art by empirical study. In one embodiment, a duty cycle of 1:4 and a 1 s cycle was utilized in our trials (that is, 200 μs of activity followed by 800 μs of "silence"). The on/off ratio and cycle duration may be varied as required or desired. Other duty cycles may be suitable, depending inter alia on the species of cell, the frequency and intensity of the ultrasound.

When several features of the present invention are combined, the resulting application may be termed "LIPUS," which refers to low-intensity pulsed ultrasound.

In one embodiment, the invention comprises the use of an ultrasound sensor, operatively connected to the ultrasound transmitter, permitting a feedback loop control over frequency and intensity. The intensity measurement can be taken with any suitable ultrasound-measuring device, which are commercially available. In one embodiment, the method further comprises the step of relaying collected information back to the ultrasonic emitter if said sensor is employed. This may be through a wired or wireless connection. A schematic representation of such a setup employing a feedback sensor is shown in FIG. 7. The feedback loop is used to maintain the ultrasound frequency and intensity at a pre-determined level or range.

Figure 1:
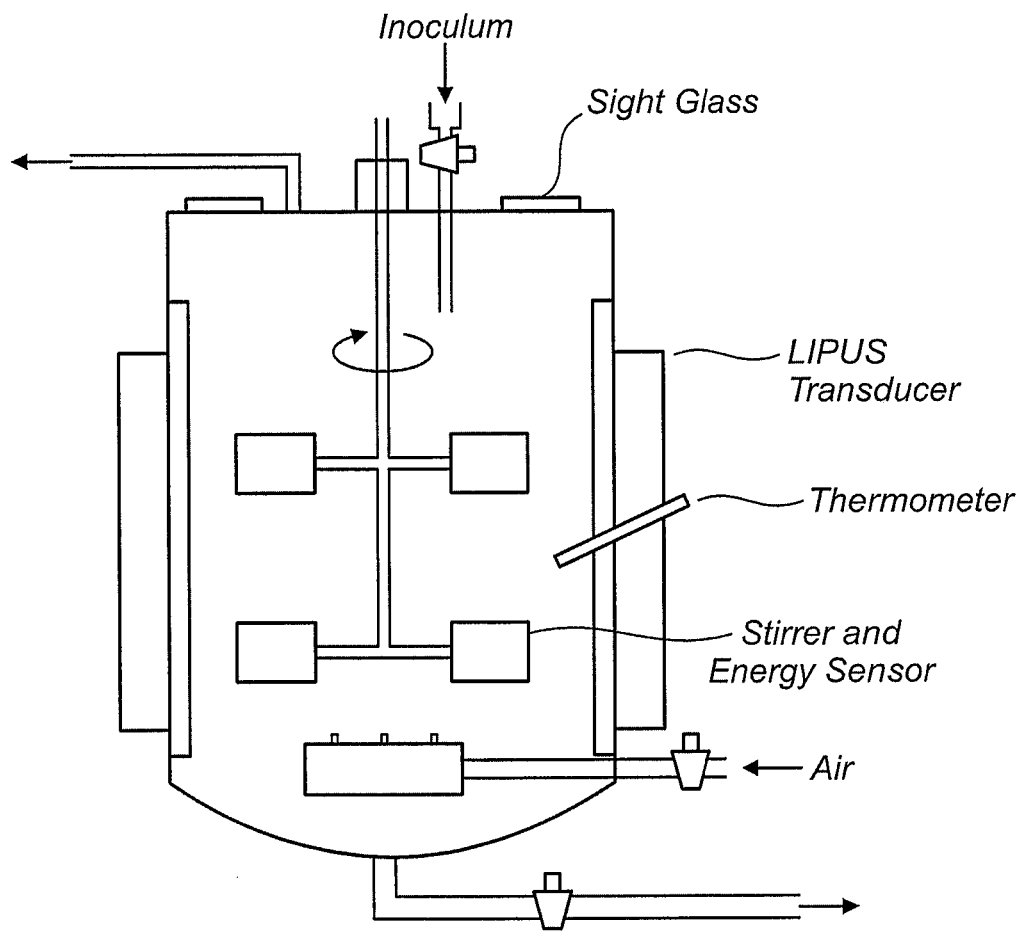
FIG. 1 is a schematic depiction of one embodiment of the invention described herein, allowing greater yield of useful biomaterials in an industrial setting. Ultrasound is applied by a piezoelectric transducer to a cell culture in a conventional fermentation tank. The transducer may be positioned to ensure maximum and uniform distribution of the ultrasound throughout the growth medium.

As mentioned above, these methods are suitable for use with cells grown in controlled and many non-controlled environments, including those in suspension. In one embodiment, where larger volumes of liquid cell culture are subjected to ultrasound, the ultrasound may be applied with a transducer array, to provide a more uniform application of ultrasound energy. As may be seen in FIG. 6, an ultrasound plate comprising a plurality of individual transducers may be disposed within a cell culture vessel. In one embodiment, the array may be disposed at the bottom of the vessel. With consistent agitation, the cell culture will be exposed to a relatively uniform amount of ultrasound energy during any application period. FIG. 6 illustrates a 5 L beaker, however, the concept may be extended fermentation tanks of significantly larger volume, such as that illustrated in FIG. 1. The design that the ultrasound emitted from the ultrasound plate generates an even amount of ultrasound across the array so that liquid in the beaker will be treated more evenly than with a single transducer at a given location.

The present invention may be embodied in other specific forms without departing from its structures, methods, or other essential characteristics as broadly described herein and claimed hereafter. The described embodiments are to be considered in all respects only as is, therefore, indicated by the appended claims, rather than by the foregoing description. All changes that come within the meaning and equivalence of the claims are to be embraced within their scope.

Exemplary embodiments of the present invention are described in the following Examples, which are set forth to aid in the understanding of the invention, and should not be construed to limit in any way the scope of the invention as defined in the claims which follow thereafter.

EXAMPLE 1

Growth of *Penicillium brevicompactum*

*P. brevicompactum* strain was obtained from Apotex Fermentation Inc. (Winnipeg, Canada). One vial of cryopreserved *P. brevicompactum* spores was diluted with sterile water (1:20). 1 ml of the spore suspension was dispensed into a 500 ml flask containing 75 ml of potato dextrose agar (PDA) and incubated for 9 days at room temperature. 50 ml of sterile 0.01% Tween™ 80 was added to the spore culture flask and the spores were scraped into solution. The solution was transferred to a sterile container. 200 µL, of the spore suspension was inoculated into a 125 ml plastic flask with 25 ml seed medium. The seed flasks were incubated at 27° C., 200 rpm (2" throw) for 48 hours. 0.5 ml of seed culture was inoculated into flasks containing 25 ml production medium and incubated at 27° C., 200 rpm (2" throw).

For Examples 4-5, *P. brevicompactum* culture was maintained on a PDA plate. For inoculation, ceorangiospores were washed from the PDA plate with sterilized water and filtered through a sterile cell strainer (catalog no. 22363549, Fisher Scientific Company, Ottawa, ON) to remove mycelia. The spore solution was diluted to $2 \times 10^6$ cells/ml to inoculate the shake flask. The flasks were incubated at 200 rpm and 23° C.

Ten minutes of ultrasound treatment were applied to the each flask everyday with different intensities. The fermentation media are set out below:

TABLE 1

Fermentation media

| | Seed Medium Amount (g/L) | Production Medium Amount (g/L) |
|---|---|---|
| Sucrose | 52.0 | 150.0 |
| Glycine | 7.5 | 14.0 |
| Yeast extract | 2.0 | 0 |
| $MgSO_4 \cdot 7H_2O$ | 1.0 | 1.0 |
| $KH_2PO_4$ | 1.0 | 1.0 |
| JEC TE solution | 1.0 ml/L | 1.0 ml/L |

The JEC trace element solution was prepared by mixing $Na_2MoO_4 \cdot 2H_2O$ (0.3 g/l), $H_3BO_3$ (2.0 g/l), $CuSO_4 \cdot 5H_2O$ (0.2 g/l), $FeSO_4 \cdot 7H_2O$ (1.714 g/l), $MnSO_4 \cdot H_2O$ (0.171 g/l), $ZnSO_4 \cdot 7H_2O$ (5.906 g/l) and citric acid (2.0 g/l). The pH of the media was adjusted to 4.5 before autoclaving.

After four days of incubation, culture were collected for MPA quantification. Extraction of MPA from the fermentation broth was carried out by adding one volume of 50% acetonitrile in water, followed by shaking at 200 rpm for 1 hour at room temperature. The extraction was centrifuged at 8000 rpm for 30 minutes. The resulting supernatant was filtrated through 0.22 µm filter and was analyzed by HPLC for MPA concentration (Example 2).

Biomass analyses were carried out according to the standard filter paper/oven method. Briefly, a pre-determined volume of culture was filtered through pre-weight filter paper. The dry cell mass was then determined by putting the filter paper in oven overnight at 65° C. The filtrate was used to determine the residual glucose in culture using the dinitrosalicylic acid method (Mandels, 1974).

Biomass production was elevated 10% and 9% in cultures treated with ultrasound at D (60 mW/cm$^2$) and E (30 mW/cm$^2$) respectively (FIG. 4).

EXAMPLE 2

MPA Quantitation by HPLC

Calibration and quality control standards were prepared by dilution of MPA stock solution with acetonitrile. Calibration standards containing 0.5, 1.0, 10, 50, 100, 250, 500 µg/ml MPA were used to construct a calibration curve using 1/×2 linear regression.

HPLC was performed using an Agilent 1100 HPLC system (Agilent Technologies, Waldbronn, Germany). The analytical column was a SymmetryShield™ RP8, 100×4.6 mm, 3.5 µm column (WAT094275, Waters Corporation, Milford, Mass.) with a SymmetryShield™ 3.9×20 mm, 5 µm guard column (WAT200675, Waters Corporation). The mobile phase consisted of buffer A (5 mM $NaH_2PO_4$ solution and methanol at a ratio of 13:7 v/v) and buffer B (2.5 mM $NaH_2PO_4$ solution and methanol at a ratio of 1:9 v/v). The pH was adjusted to 4.0 using 1.0 M phosphoric acid. Elution of MPA from the column was carried out with a linear gradient mobile phase at a flow rate of 1.0 ml/min from 0 to 80% B in 8 min, from 80% to 100% B in 4 min, 100% B kept for 4 min, from 100% B to 0% B in 1 min, and 0% B kept for 5 min. The total analysis time for each sample was thus 22 minutes. MPA absorbance was monitored at 215 nm wavelength.

MPA concentration from culture treated with ultrasound at D and E levels show a 6-14% increase in MPA production (FIG. 5).

EXAMPLE 3

Higher Intensity Ultrasound

Certain higher levels of ultrasound treatment may suppress cell growth. *P. brevicompactum* treated with 80 mW/cm$^2$ showed a slight decrease in biomass and MPA production under the specific growth conditions used, whereas ultrasound at 30 and 60 mW/cm$^2$ showed increases in biomass and MPA production (FIGS. 4 and 5).

EXAMPLE 4

Effect of Ultrasound on Cell Growth

Shake flasks (2.8 L, without baffles) containing 400 ml medium were used, with one flask being the control (without ultrasound treatment) and one flask being treated with ultrasound (intensity of 80 mW/cm$^2$ for ten minutes once daily). Samples were taken every 24 hours from the flask to test cell dry weight (FIG. 8), residual glucose (FIG. 9), and MPA production (FIG. 10).

Ultrasound treatment did not have detrimental effects on normal cell growth. During the fermentation process, the cell mass increased and then decreased; the residual glucose decreased; and the MPA concentration increased with culture time.

EXAMPLE 5

Optimization of Ultrasound Parameters to Enhance MPA Production a) Various ultrasound parameters (i.e., intensity, treatment duration, treatment frequency) were modified to assess their effects on MPA production (Table 2). The ultrasound frequency and duty cycle were kept constant. The treatment duration was fixed at ten minutes since a longer duration has no significant effect (data not shown). All experiments were conducted using 50 ml of medium in a 250 ml flask. With the exception of the control, all cultures were treated with ultrasound applied to the bottom of the flask during shaking.

TABLE 2

Effects of varying ultrasound conditions on MPA production

| Experiment No. | Intensity (mW/cm$^2$) | Time per treatment (mins) | Treatment frequency (times/day) | Final MPA concentration (mg/L) | Percentage change compared with control (%) |
|---|---|---|---|---|---|
| 1 | 80 | 10 | 4 | 1596.7 | 5.6 |
| 2 | 100 | 10 | 4 | 1560.0 | 9.0 |
| 3 | 80 | 10 | 8 | 1647.3 | 3.2 |
| 4 | 100 | 10 | 8 | 1758.9 | 16.4 |
| 5 (control) | | | | 1511.7 | |

Ultrasound treatment had a positive effect on MPA production in all of the above experimental conditions. A 100 mW/cm$^2$ intensity has a greater effect than that of 80 mW/cm$^2$. In particular, a 100 mW/cm$^2$ intensity at a duration of 10 minutes and 8 times daily increased MPA production up to 16.4%, compared 9.0% at an intensity of 100 mW/cm$^2$ for 10 minutes, 4 times daily. These results indicate that stronger ultrasound treatment (i.e., greater ultrasound intensity and more frequent treatment) induces cells to produce more MPA.

b) The ultrasound intensity was increased to 200 mW/cm$^2$ and the treatment frequency was increased to 12 times per day (Table 3). All experiments were conducted using 50 ml of medium in a 250 ml flask in duplicate, while the control experiment was conducted in triplicate. At the end of the experiment, three samples were taken from each flask and individually analyzed for MPA production.

The results indicate that the particular conditions of experiments #1 and #2 increased MPA production by 67% and 54%, respectively. Experiments #5 and #6 showed that ultrasound treatments increased MPA production by 50% and 40%, respectively. In contrast, Experiments #3 and #4 showed the opposite results. Experiment #3 increased MPA production by 13%, which is consistent with the results of part (a) in which a 16% increase was observed. Experiment #4 decreased MPA production by 6% and the MPA concentration (1204 mg/l) was similar to that of the control since the ultrasound was not effectively transferred into the culture due to lack of proper contact between the flask and transducers.

Since duplicate flasks were used for each ultrasound treatment, the average value was calculated. For the second ultrasound condition (100 mW/cm$^2$, 10 minutes per treatment, 10 treatments per day), experiment #3 was selected and the increase of MPA was calculated (FIG. 11). The results confirm that ultrasound increases MPA production. Relatively higher ultrasound intensity has a more positive effect for MPA; for example, 200 mW/cm$^2$, 8 times daily, increased MPA production by 60%, whereas 100 mW/cm$^2$, 12 times daily, increased MPA production by 45%. LIPUS (1.5 MHz and 20% duty cycle—200 μs ultrasound on and 800 μs ultrasound off) can thus enhance P brevicompactum fermentation for the production of MPA by 60% more than the control. This finding offers a possible solution to reduce the cost of making fermentation-based drugs.

TABLE 3

Effects of varying ultrasound conditions on MPA production

| Experiment # | Intensity (mW/cm$^2$) | Time per treatment (mins) | Treatment frequency (times/day) | Final MPA concentration (mg/L) | Std (mg/L) | Percentage change compared with the average control value (%) |
|---|---|---|---|---|---|---|
| 1 | 200 | 10 | 8 | 2135 | 111 | 67 |
| 2 | 200 | 10 | 8 | 1975 | 66 | 54 |
| 3 | 100 | 10 | 8 | 1452 | 57 | 13 |
| 4 | 100 | 10 | 8 | 1204 | 81 | −6 |
| 5 | 100 | 10 | 12 | 1913 | 95 | 50 |
| 6 | 100 | 10 | 12 | 1794 | 100 | 40 |
| 7 (control) | No ultrasound | | | 1305 | 94 | |
| 8 (control) | No ultrasound | | | 1288 | 120 | |
| 9 (control) | No ultrasound | | | 1244 | 53 | |
| Average of control value | | | | 1279 | 31 | |

EXAMPLE 6

Growth of *Trichoderma reesei*

The following *T. reesei* strains were used: *T. reesei* QM9414 (#843-ALK01120) and *T reesei* Rut C-30 (#844-ALK02374) (Roal Oy, 2007). The CMT method was applied for growth under 12 hrs/12 hrs light/dark conditions. A 1 mm diameter plug of fungi was taken from the original plate and inoculated on the centre of a 60 mm Petri dish, previously treated with carboxymethyl cellulose agar containing 1% Congo red dye. The plates were kept at room temperature for 2 hrs to allow the agar to solidify. Ten minutes of LIPUS treatment was applied on the fungi at 2, 4, 21, 24, 48 and 72 hrs after the initial inoculation at different intensities: 20 mW/cm$^2$ for 844 A2, 50 mW/cm$^2$ for 844 C2, and 100 mW/cm$^2$ for 844 E2. Plates were then de-stained using 1 M sodium chloride, and the relative cellulase activity was measured using the ICMC index procedure (Bradner et al., 1999; Teather and Wood, 1982) and microscopic observation.

Figure 2:
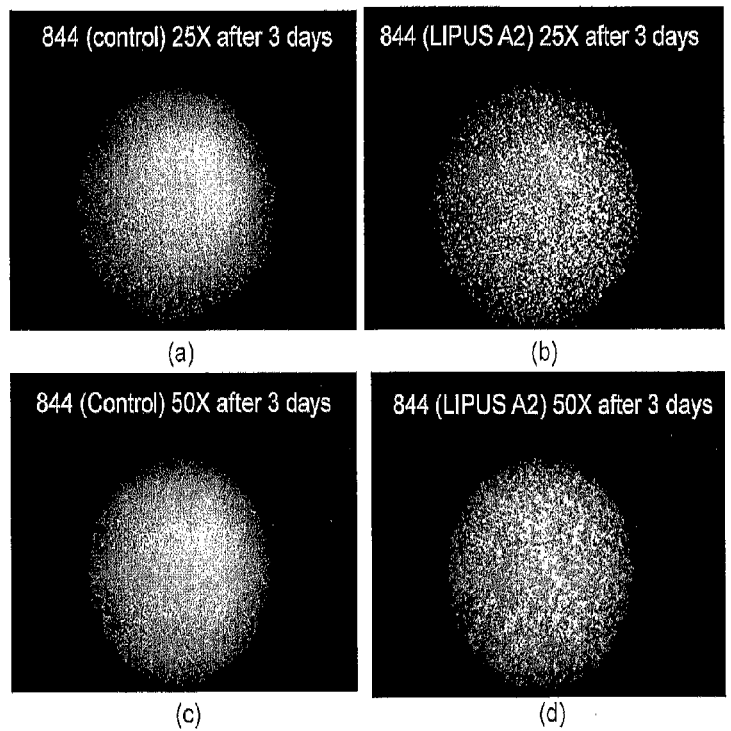
FIG. 2 shows microscopic images of a fungi (*T. reesei*) which has been stimulated with ultrasound and a control. The number of fungi is significantly increased after applying ultrasound. Identification number 844 was assigned to strand Rut-C30: (a) control after three days under 25× enlarged microscopic magnitude; (b) after three days under 25× enlargement; (c) control after three days under 50× enlargement; and (d) ultrasound after three days under 50× enlargement.
Figure 3:
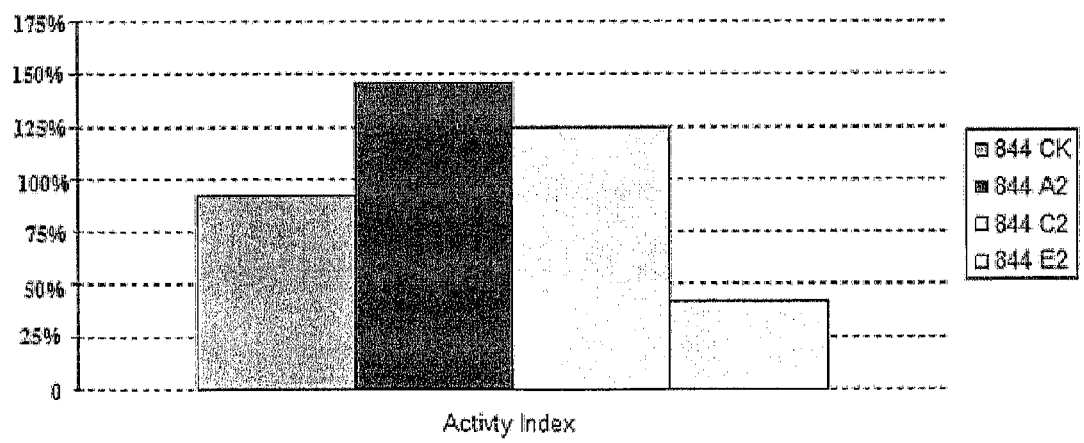
FIG. 3 is a comparison of the cellulase activity of *T. reesei* (strain Rut-C30 or 844) with and without ultrasound (844

As shown in FIG. 2, LIPUS at 20 and 40 mW/cm$^2$ stimulated culture growth compared to the control (844 CK), but higher intensities could also inhibit growth; thus, optimizing the LIPUS intensity is preferred.

EXAMPLE 7

Degradation of Cellulose to Glucose

*T. reesei* (catalog no. 56765) was obtained from American Type Culture Collection (Manassas, Va.). The fermentation medium contained KH$_2$PO$_4$ (15 g/L), (NH$_4$)$_2$SO$_4$ (5 g/L), MgSO$_4$.7H$_2$O (1.23 g/L), FeSO$_4$.7H$_2$O (0.00271 g/L), MnSO$_4$.H$_2$O (0.0016 g/L), ZnSO$_4$.H$_2$O (0.0014 g/L), CoCl$_2$.6H$_2$O (0.0036 g/L), CaCl$_2$.2H$_2$O (0.8 g/L), Tween™ 80 (0.5 g/L), yeast extract (3 g/L), peptone (0.75 g/L) and Solka-Floc™ (10 g/L). The initial pH was adjusted to 4.8.

The inoculum for the fermentation was prepared by growing the seed culture in the above medium supplemented with 5 g/L glucose for three days at 28° C. at 200 rpm. The seed culture was used to inoculate the fermentation medium as 10% of the total volume of the fermentation medium. Fermentation was conducted at 28° C. and a rotation of 200 rpm. Experimental samples were sonicated at different energy levels (or intensity) with different exposure times at different intervals, and compared for their effect on enzyme production with respect to untreated samples. LIPUS emitting transducers (1.5 MHz, 20% duty cycle) were placed underneath each of the flasks in a rotary shaker.

At the end of fermentation, 10 mL of culture was withdrawn from each flask and centrifuged for 5 minutes at 10000 rpm. The clear supernatants were assayed for filter paper cellulase activity in order to determine the amount of cellulase produced in each flask and expressed the enzyme activity as filter paper unit per mL (FPU/mL) of culture supernatant. FIG. 12 shows a graphical representation of cellulase production, and FIG. 13 shows the improvement in cellulase production under various LIPUS treatment conditions.

The highest cellulase activity was 4.93 FPU/ml and was observed in the culture sonicated at 1.5 MHz with a 20% duty cycle of 60 mW/cm$^2$ intensity for 5 minute intervals, 12 times a day. This cellulase activity is 20% higher than that observed for the control culture which received no LIPUS. This result suggests that the amount of cellulase produced in the flask that received these specific LIPUS parameters is 20% higher than the control. This also implies that the particular LIPUS treatment induces *T. reesei* to produce more cellulase.

EXAMPLE 8

Production of Ethanol from Glucose

*Saccharomyces cerevisiae* (catalog no. 96581) was obtained from American Type Culture Collection (Manassas, Va.). The fermentation medium contained glucose solution (150 g/L) supplemented with (NH$_4$)$_2$HPO$_4$ (5 g/L), MgSO$_4$.7H$_2$O (1.23 g/L), NaH$_2$SO$_4$ (1.38 g/L), and yeast extract (3 g/L). The initial pH was adjusted to 5.5 with NaOH.

The inoculum for the fermentation was prepared by growing the yeast cells in 100 ml of YPD medium for 24 hours at 30° C. at 180 rpm. The seed culture was harvested by centrifuging for five minutes at 3000 rpm, washed with 0.9% NaCl solution, and resuspended in 10 mL of fermentation broth which was used to inoculate the fermentation medium as 1% of the total volume. Fermentation was conducted at 30° C. and a rotation of 180 rpm. The LIPUS conditions are the same as described in Example 7.

Following fermentation, 1.5 ml of culture was withdrawn from each flask and centrifuged at 13000 rpm. The clear supernatants were assayed for ethanol and residual reducing sugars. The samples were treated with a Quantichrome™ DIET 500 kit to remove the residual sugar before determining the concentration of ethanol with the Quantichrome™ Ethanol assay kit. FIG. 14 is a graphical representation of the concentration of ethanol produced in each flask. FIG. 15 shows the improvement in ethanol production for individual LIPUS treatment conditions.

The highest ethanol production was observed in the culture which received a LIPUS treatment of 1.5 MHz with a 20% duty cycle of 60 mW/cm$^2$ intensity for five minutes, 12 times per day. The amount of ethanol produced in this culture was 3.65%, which is 16% higher than that observed in the control culture which received no LIPUS treatment. This result suggests that LIPUS treatment induces the *S. cerevisiae* to produce more ethanol. Ultrasound treatment which is too strong (100 mW/cm$^2$) negatively impacts ethanol production.

Lignocellulosic bio-ethanol production consists of two steps: (i) degradation of cellulose by *T. reesei* to convert lignocellulose biomass into glucose; and (ii) fermentation by *S. cerevisiae* to convert glucose into ethanol. The results of Examples 7 and 8 indicate that LIPUS can affect microorganism growth and activity. Cellulase production by *T. reesei* increased by 20% and the ethanol production by *S. cerevisiae* increased by 16% to yield a calculated improvement of 39% in overall bio-ethanol production process.

REFERENCES

The following references are incorporated herein by reference (where permitted) as if reproduced in their entirety. All references are indicative of the level of skill of those skilled in the art to which this invention pertains.

Ang, W. T.; Scurtescu, C.; Hoy, W.; El-Bialy, T.; Tsui, Y. Y. and Chen, J. (2010) Design and implementation of therapeutic ultrasound generating circuit for dental tissue formation and tooth-root healing. *IEEE Trans. Biomedical Circuits and Systems* 4(1):49-61.

Bachem, M. (2006) Ultrasound device and method of use. United States Patent Application Publication No. 2006/0106424 A1, published May 18, 2006.

Bradner, J. R.; Gillings, M. and Nevalainen, K. M. H. (1999) Qualitative assessment of hydrolytic activities in antarctic microfungi grown at different temperatures on solid media. *World J. Microbiol. Biotechnol.* 15: 131-132.

Chen, H. and Qiu, W. (2010) Key technologies for bioethanol production from lignocelluloses. *Biotechnol Adv.* 28(5): 556-562.

Doan, N.; Reher, P.; Meghji, S, and Harris, M. (1999) In vitro effects of therapeutic ultrasound on cell proliferation, protein synthesis, and cytokine production by human fibroblasts, osteoblasts, and monocytes. *J Oral Maxillofac Surg.* 57:409-419.

Duarte, L. R. (1985) Method for healing bone fractures with ultrasound. U.S. Pat. No. 4,530,360, issued Jul. 23, 1985.

Gul, H.; Xu P.; Woon, T.; Ang, M. H.; Yang, X.; Xing, J. and Chen, J. (2010) Ultrasound treatment enhances proliferation of hematopoietic stem/progenitor cells: implication for clinical transplantation, gene and cellular therapies. *Annual Conference of International Society for Cellular Therapy*, Philadelphia, Pa., May 25.

Khanal, S. K.; Montalbo, M.; van Leeuwen, J.; Srinivasan, G. and Grewell, D. (2007) Ultrasound enhanced glucose release from corn in ethanol plants. *Biotechnol Bioeng.* 98(5):978-985.

Kobayashi, Y; Sakai, D.; Iwashina, T.; Iwabuchi, S, and Mochida J. (2009) Low-intensity pulsed ultrasound stimulates cell proliferation, proteoglycan synthesis and expression of growth factor-related genes in human nucleus pulposus cell line. *Eur. Cell Mater.* 17: 15-22.

Leung, K. S.; Lee, W. S., Tsui, H. F.; Liu, P. P. and Cheung, W. H. (2004) Complex tibial fracture outcomes following treatment with low-intensity pulsed ultrasound. *Ultrasound Med. Biol.* 30:389-395.

Mandels, M. (1974) Production and Applications of Cellulase. Laboratory Procedures Handbook, U.S. Army Materials Laboratories.

Min, B. H.; Woo, J. I.; Cho, H. S.; Choi, B. H.; Park, S. J.; Choi, M. J. and Park, S. R. (2006) Effects of low-intensity ultrasound (LIPUS) stimulation on human cartilage explants. *Scand J Rheumatol.* 35:305-311.

Osawa, K.; Okubo, Y.; Nakao, K.; Koyama, N. and Bessho K. (2009) Osteoinduction by microbubble-enhanced transcutaneous sonoporation of human bone morphogenetic protein-2. *J Gene Med.* 11: 633-641.

Pandey, A. (2008) Handbook of Plant-Based Biofuels. CRC Press.

Pitt, W. G. and Ross, S. A. (2003) Method to increase the rate of cell growth. United States Patent Application Publication No. 2003/0153077 A1, published Aug. 14, 2003.

Rubin, C.; Bolander, M.; Ryaby, J. P. and Hadjiargyrou, M. (2001) The use of low intensity ultrasound to accelerate the healing of fractures. *J Bone Joint Surg Am.* 83:259-270.

Soetaert, W. and Vandamme, E. J. (2009) Biofuels. Wiley.

Sun, J. S.; Hong, R. C.; Chang, W. H.; Chen, L. T.; Lin, F. H. and Liu, H. C. (2001) In vitro effects of low-intensity ultrasound stimulation on the bone cells. *J Biomed Mater Res.* 57:449-56.

Svetlana, N.; Ljiljana, M.; Rankin, M.; Pejin, D. and Pejin, J. (2010) Ultrasound-assisted production of bioethanol by simultaneous saccharification and fermentation of corn meal. *Food Chem.* 122: 216-222.

Teather, R. M. and Wood, P. J. (1982) Use of Congo red-polysaccharide interactions in enumeration and characterization of cellulolytic bacteria from the bovine rumen. *Appl Environ Microbiol.* 43: 777-780.

Wood, B. E.; Aldrich, H. C. and Ingram, L. O. (1997) Ultrasound stimulates ethanol production during the simultaneous saccharification and fermentation of mixed waste office paper. *Biotechnol Progress* 13(3):232-237.

Yang, F.; Li, L.; Li, Q.; Tan, W.; Liu, W. and Xian, M. (2010) Enhancement of enzymatic in situ saccharification of cellulose in aqueous-ionic liquid media by ultrasonic intensification. *Carbohydrate Polymers* 81 (2): 311-316.

Yoon, J. H.; Roh, E. Y.; Shin, S.; Jung, N. H.; Song, E. Y.; Lee, D. S.; Han, K. S.; Kim, J. S.; Kim, B. J.; Jeon, H. W. and Yoon K. S. (2009) Introducing pulsed low-intensity ultrasound to culturing human umbilical cord-derived mesenchymal stem cells. *Biotechnol Lett.* 31:329-335.

Zhou, S.; Schmelz, A.; Seufferlein, T.; Li, Y.; Zhao, J. and Bachem, M. G. (2004) Molecular mechanism of low intensity pulsed ultrasound in human skin fibroblast. *J Biol. Chem.* 279:54463-54469.

What is claimed is:

1. A method of increasing the rate of growth, useful product production, or protein expression of a microorganism, comprising:
   exposing the microorganism to ultrasound having a frequency from greater than about 1 MHz to about 10 MHz, wherein the microorganism comprises yeast.

2. The method of claim 1 wherein the ultrasound is pulsed.

3. The method of claim 2, wherein the frequency of the ultrasound is from greater than about 1 MHz to 2 MHz.

4. The method of claim 3, wherein the frequency of the ultrasound is between about 1.4 MHz and about 1.6 MHz.

5. The method of claim 4 wherein the frequency of the ultrasound is about 1.5 MHz.

6. The method of claim 1 wherein the ultrasound is applied in periodic intervals.

7. The method of claim 1, wherein the ultrasound is pulsed, the frequency of the ultrasound is between about 1.4 MHz and about 1.6 MHz, and the ultrasound is applied in periodic intervals.

8. The method of claim 1, wherein the microorganism is *Saccharomyces cerevisiae*.

9. A method of increasing the rate of growth, useful product production, or protein expression of a microorganism, comprising
   exposing the microorganism to ultrasound having a frequency from greater than about 1 MHz to about 10 MHz, wherein the microorganism comprises a protist.

10. The method of claim 9 wherein the ultrasound is pulsed.

11. The method of claim 9, wherein the frequency of the ultrasound is from greater than about 1 MHz to 2 MHz.

12. The method of claim 9, wherein the frequency of the ultrasound is between about 1.4 MHz and about 1.6 MHz.

13. The method of claim 9 wherein the frequency of the ultrasound is about 1.5 MHz.

14. The method of claim 9 wherein the ultrasound is applied in periodic intervals.

15. The method of claim 9, wherein the ultrasound is pulsed, the frequency of the ultrasound is between about 1.4 MHz and about 1.6 MHz, and the ultrasound is applied in periodic intervals.

* * * * *

UNITED STATES PATENT AND TRADEMARK OFFICE
CERTIFICATE OF CORRECTION

PATENT NO. : 9,012,192 B2
APPLICATION NO. : 13/238978
DATED : April 21, 2015
INVENTOR(S) : Jie Chen et al.

It is certified that error appears in the above-identified patent and that said Letters Patent is hereby corrected as shown below:

Title Page

In References Cited:

Page 2, Item (56)

Col. 1, line 34, please delete "A."
Col. 1, line 35, please delete ""Handbook of Plant-Based Biofuels"," and insert --Handbook of Plant-Based Biofuels,--

Col. 2, line 12, please delete "Gamauf." and insert --Gamauf,--

Page 3, Item (56)

Col. 2, line 4, please delete "$CD34^+CD38$" and insert --$CD34^+CD38^-$--
Col. 2, line 46, please delete "Wetner" and insert --Werner--

Signed and Sealed this
Fourth Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 9,012,192 B2  
APPLICATION NO. : 13/238978  
DATED : April 21, 2015  
INVENTOR(S) : Jie Chen et al.

Page 1 of 1

It is certified that error appears in the above-identified patent and that said Letters Patent is hereby corrected as shown below:

In References Cited:

Title Page Item (56) under Other Publications

Col. 2, line 1, please delete "Untrasound" and insert --Ultrasound--

Signed and Sealed this

Thirteenth Day of October, 2015

Michelle K. Lee
*Director of the United States Patent and Trademark Office*